(12) United States Patent
Tamura

(10) Patent No.: US 6,333,160 B1
(45) Date of Patent: Dec. 25, 2001

(54) METHOD AND SPECIFIC DIAGNOSTIC SYSTEM FOR OBJECTIVELY ASSESSING AND MONITORING THE RELATIVE HOMEOSTASIS AND HEALTH OF ANIMALS

(76) Inventor: Keiji Tamura, No. 34-8, 6-chome, Sakuragaoka Sendai-shi, Miyagi-Ken 980 (JP)

( * ) Notice: Subject to any disclaimer, the term of this patent is extended or adjusted under 35 U.S.C. 154(b) by 0 days.

(21) Appl. No.: 08/041,428

(22) Filed: Mar. 31, 1993

Related U.S. Application Data

(63) Continuation-in-part of application No. 07/700,958, filed on May 14, 1991, now abandoned, which is a continuation-in-part of application No. 07/263,349, filed on Oct. 27, 1998, now abandoned.

(30) Foreign Application Priority Data

Aug. 31, 1988 (JP) .................................................. 63-217992

(51) Int. Cl.$^7$ .................................................. G01N 33/53
(52) U.S. Cl. ............................ 435/7.1; 436/501; 436/518
(58) Field of Search ........................... 435/7.1, 967, 975; 436/64, 804, 811, 813, 815, 822, 501, 518, 538; 530/395, 829, 832

(56) References Cited

U.S. PATENT DOCUMENTS

| | | |
|---|---|---|
| 4,215,109 | 7/1980 | Ruhenstroth-Bauer .............. 424/177 |
| 4,492,753 | 1/1985 | Shell et al. .............................. 435/17 |
| 4,801,533 | 1/1989 | Fudenberg ............................... 435/7 |

FOREIGN PATENT DOCUMENTS 0199196    4/1986   (EP) .

OTHER PUBLICATIONS

Taira et al., Isolation & Characterization of alpha1–acid glycoprotein from horses, AmJ. Vet. Res., vol. 53, No. 6, 961–65 (Jun. 1992).
Motoi et al., Correlation of serum concentration of alpha-1-acid glycoproptein with lymphocyte blastogenesis, AmJ. Vet. Res., vol. 53, No. 4, 574–79 (Apr. 1992).
Yokyoyama et al., Serum alphal–acid glycoprotein in Cattle with various diseases, J.Jpm.Vet.Med.Assoc., 42, 90–93 (1989).
Itoh et al., A case of bovine skin leukosis regressing spontaneously, J.Jpn.Vet.Med.Assoc., 42, 116–19 (1989).
Oonaru et al., Serum alphal–acid glycoprotein in castle with neoplasticc diseases, J.Jpn.Vet.Med.Assoc., 43, 19–23 (1990).
Vansickle, Sizing up Stress in the Hog House, Nat'l Hog Farmer 30–38, Jun. 15, 1992.
Eckersall, Animal Acute Phase Protein: Past, Present and Future, Vth Congress of ISACB, 97,102 (1992).
Saikin Kagaku Institute Co., Ltd., Significance of the measurement of Serum alphal–acid glycoprotein in Animals, Distributed in U.S. by DTI, Inc. (Nov. 1992).
Brochure—Bovine alphal–acid glycoprotein Plate, 6 pages, Distributed by Saikin Kagaku Institute Co., Ltd. in U.S., 2/91.
Belpaire.et al, Biological Abstracts, No. 18333, 1987, vol. 84(2), p. AB–825.
Belpaire Et Al., $\alpha_1$–Acid Glycoprotein and Serum Binding of Drugs in Healthy and Diseased Dogs. J. Vet. Pharmacol. Therap. 10:43–48, 1987.*
Stone Et Al., Cloning and Developmental Regulation of $\alpha_1$ Acid Glycoprotein in Swine. Developmental Genetics 8:295–304, 1987.*
Tamura Et Al., Isolation, Characterization, and Quantitative Measurement of Serum $\alpha_1$–Acid Glycoprotein in Cattle. Jpn. J. Vet. Sci(51(5):987–994, 1989.*
Tamura Et Al., Measurement and Signifficance of Proteins in Cow's Milk, Japanese Journal Veterinary Science Annual Meeting 110:279, 1990.*
Itoh Et Al., Serum $\alpha_1$–Acid Glycoprotein in Cattle with Inflammatory Disease and that after Operation. Jpn. J. Vet. Sci. 52(6):1293–1296, 1990.*

* cited by examiner

Primary Examiner—Donna C. Wortman
(74) Attorney, Agent, or Firm—Nixon Peabody LLP; Jeffrey L. Costellia

(57) ABSTRACT

A method for objectively assessing and monitoring the relative health and homeostatic balance of a group of animals or the individual animals in the group as a basis for animal management decisions is provided. The objective assessment and monitoring method quantitatively determines the upper limit of normal for $\alpha_1$-acid glycoprotein values in a selected body fluid of a selected species of animals. The $\alpha_1$-acid glycoprotein levels of the animals to be evaluated are quantitatively determined and compared with the normal $\alpha_1$-acid glycoprotein upper limit to identify animals whose immune systems or health has been compromised by stress or disease to provide a basis for animal management decisions to promote and maintain the optimum health and well being of the group.

24 Claims, 2 Drawing Sheets

Distribution of serum $\alpha_1$AG levels in healthy cattle

Distribution of serum $\alpha_1$AG levels by sex in healthy cattle

Holstein (1~12 years old)
Mean ± SD=283.2± 82.3 (μg/ml)

- Bulls (n=95)
- Cows (n=57)
- Total (n=152)

upper limit of normal values
(450 μg/ml)

intravenous injection of 0.1ml of BCG
($10^5$ cells of BCG/mice)

METHOD AND SPECIFIC DIAGNOSTIC SYSTEM FOR OBJECTIVELY ASSESSING AND MONITORING THE RELATIVE HOMEOSTASIS AND HEALTH OF ANIMALS

This is a continuation-in-part of Ser. No. 07/700,958, filed May 14, 1991, abandoned, which is a continuation-in-part of Ser. No. 07/263,349, filed Oct. 27, 1988, now abandoned.

TECHNICAL FIELD

The present invention relates generally to a method for the assessment of the relative health and homeostatic status of animals and specifically to an objective method for assessing and monitoring the relative health and homeostatic balance of animals as a basis for effective animal management and to a specific diagnostic system for conducting the assessment and monitoring method.

BACKGROUND OF THE INVENTION

Veterinarians, live stock breeders, herd managers and others involved in the field of animal management have long sought an efficient objective way to monitor the relative health and disease states and homeostatic balance of groups of animals and to assess the relative health and homeostatic balance of a group of animals or individual animals as a basis for effective animal management decisions. Groups of animals, whether a newborn litter of piglets or a herd of dairy cattle, must be effectively managed to maintain the group in the healthiest condition possible. In addition, it is highly desirable to maintain animals intended for the commercial market as stress-free and as homeostatically balanced as possible. If the health and homeostatic balance of the group is not maintained, at best, the animals in the group will not provide commercially usable products and, at worst, the animals in the group will die. Neither situation is desirable.

The health and homeostatic balance of individual animals also provides important information required for effective animal management. Consequently, an objective method for quickly determining the relative health homeostatic status of individual animals and of the individual animals in a group so that the changes necessary to ensure that the health and homeostatic balance of both the individual animals and the group is maintained at an optimum level would be a helpful animal management tool. In the past, animal managers have been required to rely on their own experience to evaluate an animal subjectively. Such a subjective evaluation is almost always based on the observation of symptoms indicative of some clinical disease process. However, by the time observable symptoms have appeared, it is often too late to implement management decisions that will promote or maintain the optimum health and homeostatic balance of either the group or the individual animals in the group.

Livestock, such as cattle, pigs, horses, sheep, goats, fowl and the like must be kept healthy by the producer to maintain the quality of the meat, milk, eggs and other products both at levels required by various regulatory agencies and at levels acceptable to consumers so that these products meet standards for human consumption and commercial salability. From the time such animals are born until they reach the stage where they are able to produce milk or eggs or they can be slaughtered for their meat, the optimum health and homeostatic balance of the animals should be maintained. A group of healthy, homeostatically balanced animals will grow and thrive and respond positively to shipping, environmental changes, routine vaccinations and other potentially stressful situations. A group of animals which includes animals that are not healthy or which has had its homeostatic balance upset will not respond positively to these stress inducers or disease. An efficient way to assess objectively the relative health and homeostatic balance of the individual animals in a group would provide the animal manager with a basis for making decisions that will promote optimum animal health and homeostatic balance and, in turn, produce high quality animal products.

In the past, veterinarians and animal managers such as herdsmen and breeders have not had an objective method for evaluating animal health or homeostatic balance, but have been required initially to evaluate their animals' health subjectively based on their own experience and then consult with a veterinarian to obtain an accurate assessment of an animal's health. Not only is this a time-consuming and costly method, but a disease condition or response to stress is highly unlikely even to be noticed until it has advanced enough to produce observable symptoms. By this time the health of other animals in the group may have been compromised, and information relating to the relative health status of the group has been obtained too late to permit the most effective action to be taken to maintain the optimum health of the group.

Animals, such as rabbits, guinea pigs, mice, dogs, cats and rats, used for experimental investigation have also been evaluated subjectively to ascertain relative health status prior to use in a study. Typically, a change in body weight is the primary indication of an experimental animal's relative health. However, this is not the most accurate indication of relative health. An efficient and accurate objective evaluation has not heretofore been proposed for determining the health or homeostatic balance of experimental animals. Such an evaluation would both prevent the unexpected premature death of unhealthy experimental animals and insure that the animals selected for a study would remain healthy during the course of an experiment so that meaningful data will be produced.

There is, moreover, no currently available efficient method for objectively evaluating the relative health of animals kept as pets.

The presence of a disease or other abnormal condition in humans and animals generally causes changes in various components of the blood, including cell count and the distribution or concentration of serum proteins, enzymes and hormones. Changes in plasma or serum proteins called acute phase reactants have been observed in several human disease conditions. The concentrations of such proteins may increase or decrease, depending on the type of disease or abnormal condition. This information has been useful in the diagnosis and treatment of certain human disease states.

One of the acute phase reactants, $\alpha_1$-acid glycoprotein, usually increases in some disease conditions, most notably in inflammatory diseases. When a human or animal host is infected with a microbion, the host reaction is primarily an inflammatory reaction process. This process produces immunocytes, including T cells and macrophages, in response to such inducers as lipopolysaccharides, bacteria and viruses. Mediators, including tissue necrosis factor (TNF) and cytokines are produced. These mediators affect the production of serum proteins and enzymes by the hepatocytes. Some serum proteins and enzymes kill cells, while others suppress overactive immune activity. $\alpha_1$-acid glycoprotein affects T cells or macrophages to suppress immune response. The resulting immunosuppression and reduced immunity may eventually produce observable clinical symptoms of a disease condition. However, the immune system may be suppressed and symptoms never observed because of the action of active portions of the immune system, including killer cells and macrophages.

Elevated serum $\alpha_1$-acid glycoprotein levels have been found to accompany certain human disease conditions, such as, for example, ischemic cardiac events (U.S. Pat. No. 4,492,753 to Shell) and Alzheimer's Disease, cancer and pregnancy (U.S. Pat. No. 4,801,533 to Fudenberg and European Patent Publication No. 199,196 to Kuraray Co., Ltd.). The prior art has also suggested a relationship between artificially induced and naturally occurring inflammatory conditions and elevated serum $\alpha_1$-acid glycoprotein levels in some animals. U.S. Pat. No. 4,215,109 to Ruhenstroth-Bauer et al, for example, discloses that the serum concentrations of several plasma proteins, including $\alpha_1$-acid glycoprotein, increased in response to the injection of inflammation-producing compounds into rats. However, Ruhenstroth-Bauer et al is concerned primarily with the therapeutic potential of the plasma proteins in response to an inflammatory condition. Belpaire et al, in *Biological Abstracts* No. 18333, 1987, Vol. 84(2), p. AB825, describes a study of healthy dogs and dogs with inflammatory diseases, wherein the dogs with inflammatory diseases had higher serum levels of $\alpha_1$-acid glycoprotein. However, neither Ruhenstroth-Bauer et al nor Belpaire et al suggests a method for objectively evaluating a group of animals to monitor the relative health or homeostatic balance of the group or the animals in the group using $\alpha_1$-acid glycoprotein or any other objective indicator of relative health. Moreover, information relating to $\alpha_1$-acid glycoprotein levels has not specifically been applied or otherwise used objectively to monitor the relative health and/or homeostatic balance of a single animal or a group of animals, to maintain such animals in a condition of optimum health and well-being, or to provide a basis for management decisions so that such animals will be managed as effectively as possible.

The prior art, therefore, has failed to provide an effective and objective method for monitoring the relative health and homeostatic balance of individual animals or a group of animals to provide a basis for management decisions that will insure the maintenance of the optimum health and well-being of the animals. The prior art has further failed to provide an animal management method for effectively assessing the relative health and homeostatic balance of animals which determines the $\alpha_1$-acid glycoprotein levels of specific kinds of animals to accurately identify animals with compromised immune systems at an early stage. The prior art has additionally failed to provide a diagnostic system for accurately measuring the $\alpha_1$-acid glycoprotein levels in a selected body fluid of specific animals as an indicator of an adverse response to stress or disease. A need in the animal management industry exists for such methods and system.

SUMMARY OF THE INVENTION

It is a primary object of the present invention, therefore, to overcome the disadvantages of the prior art and to provide an effective, accurate and objective method for monitoring the relative health and/or homeostatic balance of individual animals or a group of animals to provide a basis for effective animal management decisions to insure and maintain the optimum health and well-being of the animals.

It is another object of the present invention to provide an objective method for monitoring the relative health and homeostatic balance of a group of animals which identifies the animals with compromised immune systems prior to the appearance of clinical signs or symptoms of a disease condition.

It is a further object of the present invention to provide information about the relative health and homeostatic balance of the animals in a group which provides an objective basis for decisions related to the optimum management of groups of animals.

It is yet another object of the present invention to provide an efficient, accurate and objective method for monitoring the management of a group of animals to enhance the productivity of the animals.

It is yet a further object of the present invention to provide an easy and accurate species-specific method for measuring the $\alpha_1$-acid glycoprotein level in the body fluids of different types of animals, including livestock, laboratory animals and pets, as an objective indication of the relative health and homeostatic balance of the animal.

It is still another object of the present invention to provide a convenient and accurate method for measuring the $\alpha_1$-acid glycoprotein level in a selected body fluid of a selected species of animal.

It is still a further object of the present invention to provide a primary diagnostic system for detecting and measuring the $\alpha_1$-acid glycoprotein level in a selected body fluid of a selected species of animal.

The aforesaid objects are achieved by providing an effective and accurate objective method for monitoring the relative health and homeostatic balance of individual animals and of a group of animals to enable the animal manager to make the management decisions required to maintain the health and well-being of the animals at an optimum level. The method of the present invention enables the animal manager to ascertain the health of individual animals in the group and take whatever action is required, such as segregating the healthy from the unhealthy animals or changing the animals' environment, to optimize the health and well-being of the whole group. The method of the present invention includes monitoring health and homeostatic status by determining quantitatively the $\alpha_1$-acid glycoprotein levels in a selected type of body fluid of all or a representative sample of the animals in the group and comparing the $\alpha_1$-acid glycoprotein level in the selected type of body fluid for each animal tested to a predetermined normal value for the same type of body fluid in the same animal species to ascertain the relative health and homeostatic balance of each animal tested and using this information as a basis for assessing the management of the animals and making management decisions. The health status of a representative sample of the animals in the group can be screened by determining the $\alpha_1$-acid glycoprotein level in a selected type of body fluid for a selected number of animals in the group to determine whether each animal's $\alpha_1$-acid glycoprotein level is within limits established to be normal for the type of body fluid and species of animal being evaluated. The relative health of the entire group can be assessed from the health of the representative sample. The present invention additionally provides a method for efficiently and accurately determining $\alpha_1$-acid glycoprotein levels in body fluids of specific species of animals and a species-specific diagnostic system for use in quantitatively determining the $\alpha_1$-acid glycoprotein in a selected body fluid.

Other objects and advantages will be apparent from the following Description, claims and Drawings.

DETAILED DESCRIPTION OF THE INVENTION

Figure 1A:
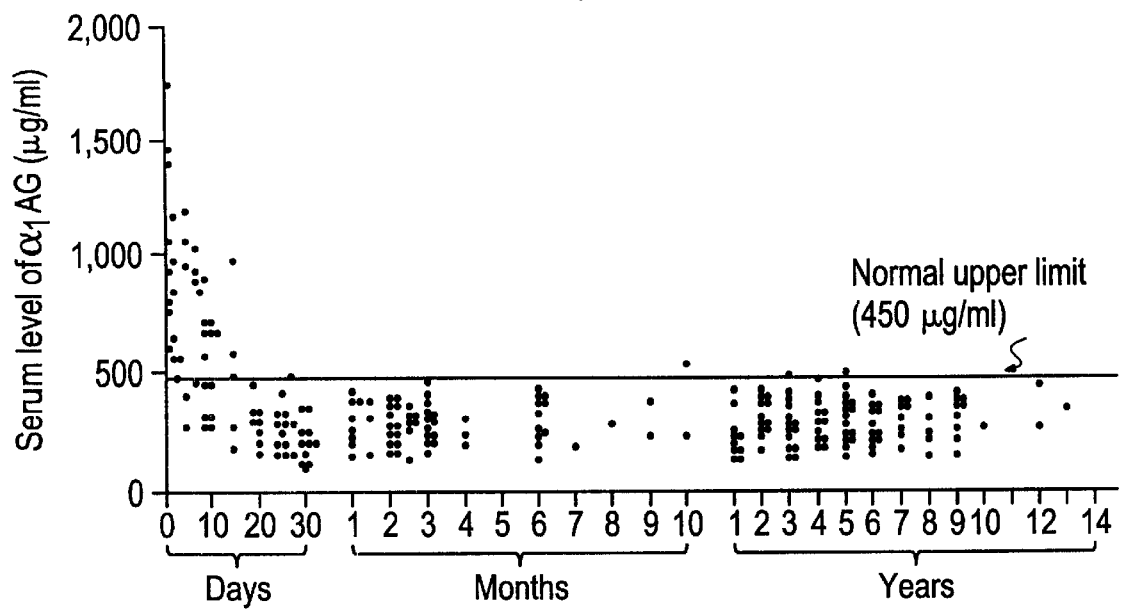
FIGS. 1A and 1B graphically represent the distribution of serum $\alpha_1$-acid glycoprotein values in healthy cattle by age and sex.

The present invention provides an efficient, effective and accurate method of objectively evaluating or screening individual animals or the animals in a group to determine the relative health status of the animals or of the group as a whole. It is possible with the present method to ascertain the general health or well-being of a group of animals by evaluating a representative sample of animals in the group. Alternatively, each animal in the group may be evaluated to determine the health status or homeostatic balance of individual animals. This information can be used as a basis for making decisions regarding management of the group of animals to promote the optimum health and well-being of the group. For example, a representative sample of the animals in the group can be evaluated objectively according to the method of the present invention to enable the animal manager to evaluate the management methods being used and to make any changes necessary for the general well-being of the group. In addition, an individual animal determined by the method of the present invention to have a compromised immune system or to be unhealthy can be removed from the group, evaluated further and treated as required. The animal manager has an objective basis for, among other things, managing a herd of animals to increase productivity, detecting early disease problems, insuring that vaccinations are given when optimum immunity can be achieved, monitoring the effectiveness of treatment methods, and assessing the impact of stress-producing conditions on a group of animals. In addition, the slaughterhouse manager has an antemortem method for assessing the health of the animals whose body parts are to be marketed for food products.

The method of the present invention enables an animal manager, who is usually not a trained veterinarian, to evaluate objectively a group of animals, which to the untrained eye appears to be normal and healthy, and determine whether the animals are, in fact, normal and healthy. The present method permits the ready identification of the unhealthy animals in a group so that the animal manager can make management decisions that benefit both the entire group and the animal whose health is found to be compromised. Animals found not to be healthy by the method of the present invention can then be referred to a veterinarian for specific diagnosis and treatment. The present method is an effective screening method for objectively evaluating the relative health and well-being of many different sizes of animal groups from litters of newborns to large herds. This method, moreover, can be used to evaluate the relative health and homeostatic balance of virtually any kind of mammal or bird.

The objective evaluation of the relative health and homeostatic balance of a group of animals according to the present invention is based on the inventor's observation that the level of $\alpha_1$-acid glycoprotein in body fluids of animals increases beyond a level determined to be normal for a selected body fluid in a particular species of animal under certain conditions, including illness, stress and homeostatic imbalance. Evaluation of the $\alpha_1$-acid glycoprotein level can indicate that an animal's immune system is compromised, even if the animal appears to be healthy. An elevated $\alpha_1$-acid glycoprotein level, however, is not necessarily indicative of a specific disease process, but may be a response to internal or environmental stress. Not every animal with an $\alpha_1$-acid glycoprotein level above normal will develop observable symptoms. However, an abnormal $\alpha_1$-acid glycoprotein level is a clear indication of a compromised immune system. Although not every animal with observable symptoms diagnosed to have a specific disease condition will demonstrate an elevated $\alpha_1$-acid glycoprotein level, the vast majority of unhealthy or homeostatically imbalanced animals will show increased $\alpha_1$-acid glycoprotein levels. Consequently, the $\alpha_1$-acid glycoprotein values in animal body fluids provide important information about the relative health and homeostatic balance of the animal.

Some acute phase proteins, including $\alpha_1$-acid glycoprotein, are elevated in the presence of disease conditions and stress. These proteins have immunosuppressive functions and assist in restoring the homeostatic balance altered by injury, tissue necrosis or infection. $\alpha_1$-acid glycoprotein levels increase when the homeostatic balance is upset. As a result, $\alpha_1$-acid glycoprotein is particularly useful as an indicator for detecting the existence of a condition, such as illness, which has upset the homeostatic balance. The inventor of the present invention has investigated $\alpha_1$-acid glycoprotein levels in the blood and other body fluids of several species of animals and has determined that these animals, as well as humans, demonstrate an increase in the level of $\alpha_1$-acid glycoprotein when their homeostatic balance has been upset by stressors such as disease, adverse environmental conditions and the like. This information can be used first to identify the presence of a stressor, secondly to identify the specific stressor and, finally, to identify conditions which produced the stressor so that such conditions can be changed.

For this purpose, the inventor of the present invention has produced, as will be described in detail below, a diagnostic system which includes anti-$\alpha_1$-acid glycoprotein serum that has a high titer and is highly specific for the species of animal to be evaluated.

Briefly, the objective method of evaluating the relative homeostasis and, therefore, the health and well-being of a group of animals or an individual animal is as follows: A diagnostic system which includes an antiserum specific for the $\alpha_1$-acid glycoprotein of the species of animals to be screened or evaluated is prepared. A sample of a selected type of body fluid is reacted with the specific antiserum, and the level of $\alpha_1$-acid glycoprotein in the body fluid is quantitatively determined to obtain the level of $\alpha_1$-acid glycoprotein in the selected type of body fluid. The level of $\alpha_1$-acid glycoprotein in the body fluid is compared to a predetermined normal $\alpha_1$-acid glycoprotein level for the selected body fluid in the species of animal being evaluated to determine whether the $\alpha_1$-acid glycoprotein is within the predetermined normal value or is abnormal. The relative health or homeostasis of the animals is assessed by identifying the animals with $\alpha_1$-acid glycoprotein levels at or below the predetermined normal value. Animals with $\alpha_1$-acid glycoprotein levels above the predetermined normal value can be specifically identified and evaluated further to ascertain the specific cause of the elevated $\alpha_1$-acid glycoprotein level.

The accurate measurement of $\alpha_1$-acid glycoprotein levels in animal body fluids requires a highly purified $\alpha_1$-acid glycoprotein to prepare the species-specific antiserum required for this purpose. The diagnostic system of the present invention includes a suitably highly purified $\alpha_1$-acid glycoprotein from a particular species of animal prepared by a quaternary purification process which includes the following steps:

A. Primary Purification By Ammonium Sulfate Fractionation

Ammonium sulfate is added to the serum obtained from a selected species of animal until 60% saturation is attained. The mixture is left at room temperature for 3 hours and the precipitate which forms is removed. Additional ammonium sulfate is added to the supernatant to attain 90% saturation. This mixture is left at 4° C. for 16 hours, and $\alpha_1$-acid glycoprotein is obtained as the precipitate.

B. Secondary Purification By DEAE-Column Chromatography

The $\alpha_1$-acid glycoprotein precipitate obtained by ammonium sulfate fractionation in Step A is dialyzed with 0.02M acetate buffer solution (pH 4.3) and is passed through a DEAE-cellulose column equilibrated with the same buffer solution. Elution is performed stepwise by changing the concentration of buffer solution, for example, to 0.1M, 0.5M and 2.0M buffer solution. $\alpha_1$-acid glycoprotein is obtained as the fraction eluted with 0.5M buffer solution.

C. Tertiary Purification By CM-Column Chromatography

The fraction of $\alpha_1$-acid glycoprotein purified through the DEAE-cellulose column in Step B is dialyzed with 0.02M acetate buffer solution (pH 4.3) and is passed through a CM-cellulose column equilibrated with the same buffer solution. $\alpha_1$-acid glycoprotein is obtained as the fraction eluted without being adsorbed. The $\alpha_1$-acid glycoprotein fraction is dialyzed with purified water and freeze-dried.

D. Quaternary Purification By Gel Filtration

The $\alpha_1$-acid glycoprotein fraction purified by the CM-cellulose column in Step C is separated according to molecular weight in a column with Sephacryl gel. The $\alpha_1$-acid glycoprotein fraction is eluted at the molecular weight of about 50,000. The $\alpha_1$-acid glycoprotein fraction is dialyzed with purified water, and is freeze-dried to obtain a white powder, which is highly purified $\alpha_1$-acid glycoprotein.

Table I presents the physicochemical properties of $\alpha_1$-acid glycoprotein isolated from the serum of various kinds of animals and purified according to the foregoing quaternary purification process.

TABLE I

| ANIMAL | MOLECULAR WEIGHT | CARBOHYDRATE CONTENT | ISOELECTRIC POINT |
|---|---|---|---|
| cattle | 38000–49000 | 26.5–47.5 | 3.0–3.8 |
| pig | 47000–50000 | 25.8–41.8 | 3.1–3.8 |
| horse | 42000–46000 | 24.6–38.2 | 3.0–3.7 |
| domestic fowl | 40000–47000 | 21.3–43.8 | — |
| dog | 31000–43000 | 22.8–43.4 | 3.0–3.9 |
| cat | 32000–42000 | 21.5–40.8 | 2.8–3.6 |
| mouse | 40000–45000 | 25.0–42.3 | 2.8–3.6 |

The diagnostic system required for the objective evaluation method of the present invention also includes a species-specific antiserum to $\alpha_1$-acid glycoprotein prepared from $\alpha_1$-acid glycoprotein isolated from a selected species of animal and highly purified by the quaternary purification process described above. Anti-$\alpha_1$-acid glycoprotein serum with high specificity and a high titer can be obtained by the present process, and a highly reliable diagnostic system can be produced.

The antiserum anti-$\alpha_1$-acid glycoprotein is prepared first by emulsifying the selected purified $\alpha_1$-acid glycoprotein with Freund's complete adjuvant and then subcutaneously injecting the emulsified $\alpha_1$-acid glycoprotein into an animal from a species different from the animal species from which the $\alpha_1$-acid glycoprotein was isolated. Injections of purified $\alpha_1$-acid glycoprotein are given repeatedly to the animal over about a two week period or until a sufficient level of antibodies to $\alpha_1$-acid glycoprotein is detected in the animal's blood. The animal's blood is then collected and centrifuged to produce a supernatant which contains antiserum specific for the $\alpha_1$-acid glycoprotein of the selected animal species.

Animals preferred for antiserum production include goats, rabbits, sheep, horses and cattle. Care must be taken, however, to insure that the animal selected for antiserum production is from a different species than the animal from which the $\alpha_1$-acid glycoprotein used to produce the antiserum was isolated.

Once a species-specific antiserum has been produced, $\alpha_1$-acid glycoprotein can be detected and quantitatively determined by any one of a number of immunological antigen-antibody reactions. The level of $\alpha_1$-acid glycoprotein in animal body fluids may be determined by single radial immunodiffusion, double immunodiffusion, immunoelectrophoresis, antigen-antibody crossed electrophoresis, counter-immunoelectrophoresis, rocket electrophoresis, sensitized hemagglutination reaction, passive hemagglutination inhibition reaction, sensitized latex agglutination reaction, turbidimetric immunoassay, radioimmunoassay, or enzyme immunoassay. Other immunological antigen-antibody reactions may also be employed for this purpose, however.

The following are exemplary immunological antigen-antibody reactions useful for quantitatively determining $\alpha_1$-acid glycoprotein values in animal body fluids in accordance with the present invention:

1. Single Radial Immunodiffusion (SRID) Method

5 $\mu$l of a specimen of the serum (antigen) to be tested for $\alpha_1$-acid glycoprotein is injected into small holes in an agar plate containing anti-$\alpha_1$-acid glycoprotein. When the reaction is performed at room temperature or at 37° C. for 24 to 48 hours, $\alpha_1$-acid glycoprotein in the specimen is diffused radially, reacts with the $\alpha_1$-acid glycoprotein antibody and forms a sedimentation or precipitin ring. Since the antigen concentration and the area of the precipitin ring are linearly related, the quantity of $\alpha_1$-acid glycoprotein in the specimen can be calculated from a calibration curve of an $\alpha_1$-acid glycoprotein standard solution. This method is easy to perform, does not require expensive equipment and instruments and has high reproducibility, but requires some time before a final quantitative evaluation of the $\alpha_1$-acid glycoprotein is available. The minimum sensitivity of this method is 5 $\mu$g/ml. The SRID method is particularly suitable for the quantitative determination of $\alpha_1$-acid glycoprotein in serum and is the preferred method for the diagnostic system of the present invention.

2. Passive Hemagglutination Inhibition Reaction (PHA-I) Method

25 $\mu$l of a buffer solution is dispensed into each well of a microplate (preferably V-type), and $2^n$ dilution series is prepared from a specimen containing $\alpha_1$-acid glycoprotein by a 25 $\mu$l diluter. 25 $\mu$l of anti-$\alpha_1$-acid glycoprotein serum with a constant titer is added to each well, mixed and left at room temperature for 30 minutes. The mixture is neutralized, 50 $\mu$l of sensitized erythrocytes (sheep erythrocytes coated with $\alpha_1$-acid glycoprotein) is added, and the mixture is left to stand for more than 2 hours, after which time the hemagglutination is evaluated. The concentration of $\alpha_1$-acid glycoprotein is calculated from the agglutination value of standard $\alpha_1$-acid glycoprotein and the dilution multiple of the specimen. This method is useful for the quantitative determination of trace amounts of $\alpha_1$-acid glycoprotein (10 µg/ml or less) and is a convenient way to measure the $\alpha_1$-acid glycoprotein in urine. However, it is not suitable for the quantitative analysis of serum $\alpha_1$-acid glycoprotein because there is considerable error in $2^n$ dilution. The sensitivity of the PHA-I method is 10 ng/ml.

3. Enzyme Immunoassay (EIA) Method

The plate method or the bead method can be used. The specimen to be tested and alkaline phosphatase-labeled $\alpha_1$-acid glycoprotein are added to material on which the antibody is coated and a competitive reaction is allowed to proceed at 37° C. for two hours. After washing, p-nitrophenyl phosphate is added, and the reaction is stopped after thirty minutes. The absorbence is measured at 450 nm. The quantity of $\alpha_1$-acid glycoprotein in the specimen is calculated from a standard curve of $\alpha_1$-acid glycoprotein similarly obtained. The sensitivity of the EIA method is 10 ng/ml.

4. Turbidimetric Immunoassay (TIA) Method

When 50 µl of $\alpha_1$-acid glycoprotein-containing specimen is added to 2.0 ml of anti-$\alpha_1$-acid glycoprotein serum diluted to a certain titer, an acid agglutination reaction occurs and turbidity results. This turbidity is enhanced by an increase in antigen or $\alpha_1$-acid glycoprotein quantity. The reaction is performed at 37° C. for 30 minutes, and turbidity is measured by a spectrophotometer (absorbance at 340 nm). After being compensated with a specimen blank value, the quantity of $\alpha_1$-acid glycoprotein is calculated from a calibration curve of $\alpha_1$-acid glycoprotein. When an automatic analyzer is used, $\alpha_1$-acid glycoprotein can be measured by the reaction at 37° C. for 10 minutes of 500 µl of antibody and 20 µl of specimen. This method can be performed quickly and has high reproducibility. The sensitivity of the TIA method is 5 µg/ml.

The method of objectively evaluating the relative homeostasis and health of a group of animals or individual animals in accordance with the present invention is illustrated by the following Examples, which are not intended to be limiting:

EXAMPLE 1

The relative health or homeostasis of a herd of cattle can be evaluated in accordance with the present invention by producing a diagnostic system which includes an antibody that is highly specific for bovine $\alpha_1$-acid glycoprotein. This diagnostic system is used first to ascertain the normal level of $\alpha_1$-acid glycoprotein in the serum of healthy cattle and then to screen other cattle to compare the serum $\alpha_1$-acid glycoprotein level of each animal screened to the normal level to determine whether each animal has a normal or abnormal $\alpha_1$-acid glycoprotein value. Cattle identified with abnormal $\alpha_1$-acid glycoprotein levels can then be evaluated further by traditional diagnostic or other methods.

Cattle were evaluated first by purifying $\alpha_1$-acid glycoprotein isolated from bovine serum and preparing a specific antiserum to bovine $\alpha_1$-acid glycoprotein. Reagents for qualitatively detecting and quantitatively determining bovine $\alpha_1$-acid glycoprotein were prepared, the level of $\alpha_1$-acid glycoprotein in normal bovine serum was detected, and the serum $\alpha_1$-acid glycoprotein in unhealthy or diseased cattle was evaluated.

A. Purification of Bovine $\alpha_1$-acid Glycoprotein

Ammonium sulfate was added to bovine serum to attain 60% saturation. After leaving it at room temperature for 3 hours, the precipitate was removed and additional ammonium sulfate was added to the supernatant until 90% saturation was reached. The solution was left at 4° C. for 16 hours to obtain $\alpha_1$-acid glycoprotein as a precipitate.

The $\alpha_1$-acid glycoprotein precipitate was dialyzed with 0.02M acetate buffer solution (pH 4.3) and was passed through a DEAE-cellulose column equilibrated by the same buffer solution. The column was washed with 0.1M buffer solution, and $\alpha_1$-acid glycoprotein was then obtained as the fraction eluted with 0.5M buffer solution.

The purified fraction of a $\alpha_1$-acid glycoprotein was dialyzed with 0.02M acetate buffer solution (pH 4.3) and passed through a CM-cellulose column equilibrated with the same buffer solution. $\alpha_1$-acid glycoprotein was obtained as the unadsorbed eluted fraction, dialyzed with purified water, and freeze-dried.

The purified freeze-dried $\alpha_1$-acid glycoprotein was fractionated according to molecular weight in a column with Sephacryl gel. The fraction of $\alpha_1$-acid glycoprotein eluted at a molecular weight of about 50,000 was dialyzed with purified water and was freeze-dried. A highly purified white powder of bovine $\alpha_1$-acid glycoprotein was obtained.

B. Preparation of Specific Antiserum to Bovine $\alpha_1$-acid Glycoprotein

Physiological saline was added to $\alpha_1$-acid glycoprotein to produce a concentration of 4 to 20 mg/ml. 0.5 to 10 ml of this solution was mixed with an equivalent amount of Freund's complete adjuvant and emulsified, and this liquid was injected subcutaneously into the back of a rabbit, although a goat could also be used. After 2 weeks, 1 to 20 ml of $\alpha_1$-acid glycoprotein similarly prepared was injected into the animal. After 2 more weeks, an additional 1 to 20 ml of emulsified solution of $\alpha_1$-acid glycoprotein was injected into the animal. On the tenth day after the last injection, blood was collected from the animal and the serum was separated. The serum was heated at 56° C. for 30 minutes and inactivated, and 0.05% sodium azide was added as a preservative. The specificity of this antiserum to bovine $\alpha_1$-acid glycoprotein was measured by Ouchterlony's method using bovine serum as the antigen and by immunoelectrophoresis. It was demonstrated that no antibodies other than anti-$\alpha_1$-acid glycoprotein were present.

C. Preparation of a Reagent to Qualitatively Test and Detect Bovine a $\alpha_1$-acid Glycoprotein Purified agar was added to 1/15M phosphate buffer in saline (pH 7.4) to attain a concentration of 1.2%. This mixture was heated, dissolved, injected into a horizontal container to a thickness of about 1.5 mm, and solidified. Holes with a 3 mm diameter and spaced about 3 mm apart were formed in the solid agar mixture. Antiserum, the bovine serum to be tested and a standard serum containing $\alpha_1$-acid glycoprotein obtained according to this invention were applied into each of these holes to fill them. The reaction was allowed to proceed at room temperature for 24 hours, after which the presence of a precipitin line between the serum to be tested and the antiserum was evaluated. When a precipitin line was observed, the test was judged as bovine $\alpha_1$-acid glycoprotein-positive.

D. Preparation of a Reagent for the Quantitative Determination of Bovine $\alpha_1$-acid Glycoprotein Purified agar was added to 1/15M phosphate buffer in saline (pH 7.4) to a concentration of 1.2%, heated, dissolved, and maintained at a temperature of 55° C. Antiserum prepared as described in Step B above was added to a final concentration of 2 to 15% and mixed. This mixture was injected into a horizontal container to a thickness of about 1.5 mm and solidified. Holes with a 3 mm diameter and spaced about 15 mm apart were formed in the solid agar mixture. 5 μl each of an original bovine $\alpha_1$-acid glycoprotein standard solution, 4× and 16× diluted solutions, and the liquid to be tested were accurately measured and were placed in the holes. When the reaction was allowed to proceed at room temperature for 24 hours, the diameter of the precipitin ring was found to correlate to the amount of $\alpha_1$-acid glycoprotein present.

E. Quantitative Determination of a $\alpha_1$-acid Glycoprotein in Normal Bovine Serum Cattle of different varieties, including Holstein, Japanese Black Cattle, Japanese Shorthorn, Hereford and Jersey were clinically screened to determine whether they appeared healthy and several biochemical blood and serum parameters were analyzed. Animals that did not appear clinically healthy or that exhibited abnormal blood and serum values were excluded from the group. The blood was examined to determine numbers of leukocytes and erythrocytes, hemochrommometry and the hematocrit. The serological biochemical examination included total cholesterol, glutamic oxaloacetic transaminase (GPT), alkaline phosphatase (ALP), γ-glutamyl transpeptidase (γ-GTP), zinc sulfate turbidity test (ZTT), total protein, serum albumin and albumin/globulin ration (A/G ratio). The use of such parameters to establish whether the parameters are normal and an animal is healthy is well known in the veterinary art. Any additional clinical, serological or like methods employed by this art to ascertain health status could also be employed, however.

The $\alpha_1$-acid glycoprotein in the serum of cattle determined as discussed above to be healthy was quantitatively evaluated by single radial immunodiffusion using the reagent prepared as described in Step D. The results are shown in Table 2.

TABLE 2

| Types of Cattle | Number of Cases | $\alpha_1$-acid glycoprotein (μg/ml) mean ± standard deviation |
|---|---|---|
| Holstein | 45 | 260 ± 88 |
| Japanese Black Cattle | 40 | 239 ± 40 |
| Japanese Shorthorn | 35 | 263 ± 82 |
| Hereford | 8 | 258 ± 158 |
| Jersey | 15 | 240 ± 98 |

The different types of healthy cattle tested showed no significant differences in $\alpha_1$-acid glycoprotein values. The maximum level of $\alpha_1$-acid glycoprotein measured in the 143 healthy cattle tested was 450 μg/ml. This value was regarded as the upper limit of normal for bovine $\alpha_1$-acid glycoprotein.

Figure 1B:
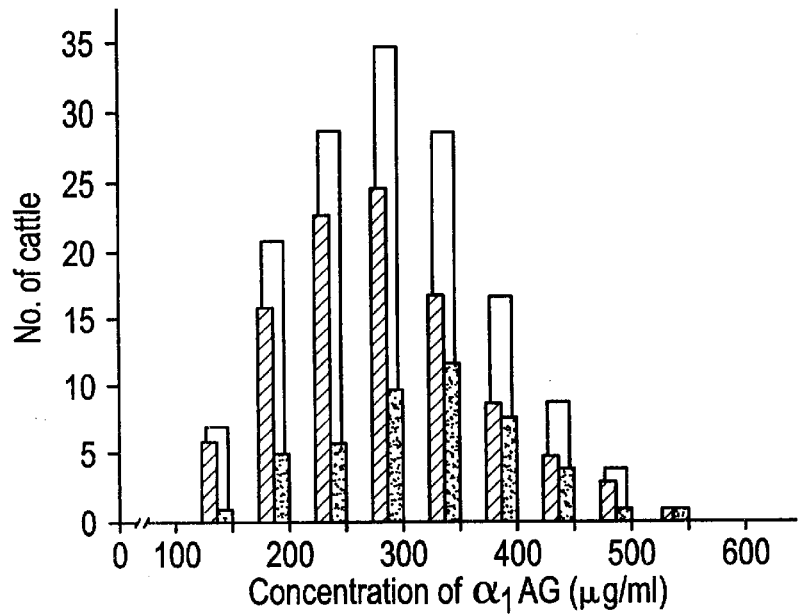

The upper limit of normal of 450 μg/ml for bovine serum $\alpha_1$-acid glycoprotein determined in the 143 healthy cattle tested as described above corresponds to the $\alpha_1$-acid glycoprotein value determined by the inventor to be the normal upper limit in other studies. FIG. 1 illustrates, graphically, the results of one such study which quantitatively measured $\alpha_1$-acid glycoprotein values in a group of 166 healthy Holstein cattle. This study demonstrated that the sex distribution for $\alpha_1$-acid glycoprotein values was relatively uniform and that there was no significant difference in $\alpha_1$-acid glycoprotein levels in bulls and cows. The mean $\alpha_1$-acid glycoprotein values for bulls and cows aged 1–12 years was 283.2±82.3 μg/ml. The mean plus two standard deviations (2 SD) for this group was 448 μg/ml. The upper limit of normal for bovine serum $\alpha_1$-acid glycoprotein was rounded to 450 μg/ml. $\alpha_1$-acid glycoprotein values higher than 451 μg/ml were regarded as abnormal.

F. Determination of $\alpha_1$-acid Glycoprotein Levels in Sick Cattle

Figure 2:
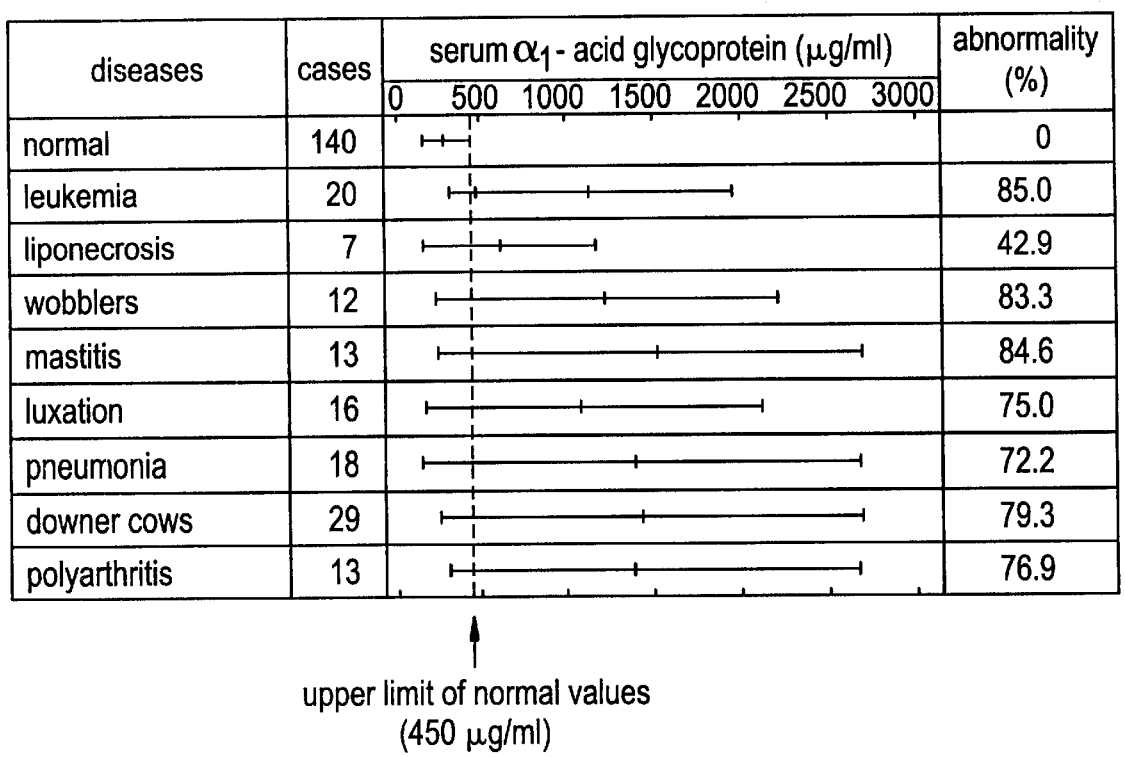
FIG. 2 is a diagram showing the range of $\alpha_1$-acid glycoprotein values in bovine serum determined by the diagnostic system of the present invention.

The serum $\alpha_1$-acid glycoprotein levels of cattle determined to be healthy as described above and the serum $\alpha_1$-acid glycoprotein levels of cattle that had been diagnosed with various bovine diseases were determined quantitatively using the reagent prepared in Step D above. These diseases included leukemia, mesenteric necrosis, wobblers, mastitis, luxation, pneumonia, downer cows and polyarthritis. The results are shown in FIG. 2. The upper value of normal for serum $\alpha_1$-acid glycoprotein was 450 μg/ml.

The abnormality ratio percentage of animals tested with $\alpha_1$-acid glycoprotein greater than the established normal value was 0%, for normal cattle, whereas that of sick cattle was: 85.0% for cattle with leukemia, 83.3% for those with wobblers, 84.6% for mastitis, 75.0% for luxation, 72.2% for pneumonia, 79.3% for downer cows, and 76.9% for polyarthritis. The unhealthy or sick cattle showed a high abnormality ratio, which demonstrates the importance to the animal manger of quantitatively determining serum $\alpha_1$-acid glycoprotein to preliminarily screen the relative health of a herd of cattle or other groups of animals. An animal with an $\alpha_1$-acid glycoprotein level above the established upper normal value which may otherwise appear healthy can be identified as unhealthy or homeostatically imbalanced by the foregoing method. This information can be used as a basis for decisions regarding the health care of the herd as well as that of individual animals determined to have elevated $\alpha_1$-acid glycoprotein levels. Animals which appear normal but have abnormal $\alpha_1$-acid glycoprotein levels can be referred to a veterinarian for diagnosis and treatment. Once a specific diagnosis has been made, the course and prognosis of the particular pathological condition identified can also be monitored by quantitatively determining and monitoring the $\alpha_1$-acid glycoprotein levels.

Additional studies conducted by the inventor have established normal bovine $\alpha_1$-acid glycoprotein values for different ages and developmental stages of cattle. At the time of calving, bovine serum $\alpha_1$-acid glycoprotein values typically range from 500 to 1500 μg/ml, but by three weeks of age the normal $\alpha_1$-acid glycoprotein level has dropped to less than 500 μg/ml. Healthy cattle from 4 weeks to 17 years of age show a fixed normal $\alpha_1$-acid glycoprotein value of from 200 to 450 μg/ml. Measurements of $\alpha_1$-acid glycoprotein levels in calves two weeks after birth demonstrated that $\alpha_1$-acid glycoprotein values in healthy calves dropped to less than 500 μg/ml, while the $\alpha_1$-acid glycoprotein values of calves diagnosed with pneumonia and other infectious diseases remained elevated.

The importance to the animal manager of monitoring $\alpha_1$-acid glycoprotein values as a basis for herd management decisions has been demonstrated by studies of cattle, including a study of Holstein bull calves fed since the fourteenth to twenty-first after birth. Blood samples were taken from the calves every 10 days, and the relationship between the appearance of disease symptoms and elevated serum $\alpha_1$-acid glycoprotein values observed. One group of calves was observed to be healthy and had normal $\alpha_1$-acid glycoprotein values (450 μg/ml or lower). A second group of calves had abnormal (elevated) $\alpha_1$-acid glycoprotein levels, but did not exhibit clinical symptoms of disease. Some of the calves with elevated $\alpha_1$-acid glycoprotein later developed pneumonia, while others did not show any clinical signs of disease. Treatment of all of these calves with antibiotics resulted in the reduction of $\alpha_1$-acid glycoprotein to normal levels. A third group of calves displayed clinical symptoms of disease and did not have abnormal acid glycoprotein values. These values were reduced after treatment, however.

Cattle with early stage hepatic abscesses have been found to show abnormal $\alpha_1$-acid glycoprotein levels. Such animals can be referred to veterinarians for specific diagnosis and the intensive treatment required to prevent the hepatic abscesses from becoming chronic.

One survey has estimated that about 16% of dairy calves dies between birth and weaning from such diseases as calf scours and pneumonia. Monitoring the $\alpha_1$-acid glycoprotein values of calves of this age allows the herd manager to identify calves with abnormal $\alpha_1$-acid glycoprotein values so that these animals can be tested further and treated appropriately. Veal calves of the same age tend to display an even greater mortality level because veal calf herds have typically been assembled from different source herds which may have used different nutrition and management programs. In addition, these calves have been subjected to such stresses as early weaning and separation, shipping and early exposure to infectious disease agents. Monitoring the $\alpha_1$-acid glycoprotein values of veal calves can advantageously be conducted both before a veal calf is shipped to market and after shipping to assess its relative health and homeostatic balance. Calves with abnormal $\alpha_1$-acid glycoprotein values prior to scheduled shipment can be retained, evaluated further, and treated prior to shipment, if indicated. Assessment of $\alpha_1$-acid glycoprotein values in veal calves after shipment identifies animals whose immune systems may have been affected by the stress of shipment or exposure to infectious diseases. These calves can then be appropriately treated. The animal health and homeostatic balance method of the present invention can enhance the quality of veal obtained from a veal calf herd by insuring that the herd is managed to maintain its optimum health and well-being.

In the following Examples, the healthy animals whose $\alpha_1$-acid glycoprotein levels were measured were determined to be healthy by clinical, hematological and serological evaluation as described above.

EXAMPLE 2

Bovine mastitis is estimated to cost the dairy industry worldwide as much as $1 billion. A great deal of effort has been expended to detect mastitis as early as possible so that appropriate treatment can be instituted at the most effective time to combat this condition as effectively as possible. The method of the present invention provides the dairy manager with an effective and highly sensitive tool for monitoring $\alpha_1$-acid glycoprotein levels in cow milk for the early detection of mastitis. $\alpha_1$-acid glycoprotein is superior in sensitivity to other serum proteins in detecting the presence of mastitis in cow milk. The milk from dairy cattle with mastitis is not commercially salable because it is not suitable for drinking and cannot be sold for human consumption. The inventor has discovered that evaluation of the level of $\alpha_1$-acid glycoprotein provides both the earliest indication of mastitis and the earliest signal of recovery after mastitis treatment is instituted. The quantitative determination of $\alpha_1$-acid glycoprotein values in cow milk was conducted according to the procedure described below.

The specific antibody to bovine $\alpha_1$-acid glycoprotein obtained as described in Paragraph B of Example 1 was coated on an insoluble carrier. Cow milk was added to this as the specimen, a marker, preferably purified $\alpha_1$-acid glycoprotein obtained as in Paragraph A of Example 1 labeled with alkaline-phosphatase was added, and a competitive reaction was performed at 37° C. for 2 hours. After washing, p-nitrophenyl-phosphate was added, and the reaction was allowed to proceed for 30 minutes, after which the absorbance was measured at 450 nm. From a standard curve of $\alpha_1$-acid glycoprotein similarly obtained, the quantity of a $\alpha_1$-acid glycoprotein in samples of cow milk was calculated. The values for $\alpha_1$-acid glycoprotein in milk from healthy cows and cows with two different types of mastitis are shown in Table 3.

TABLE 3

| Disease | Number of Cases | $\alpha_1$-acid glycoprotein (µg/ml) |
| --- | --- | --- |
| mastitis apostematosa | 10 | 10–680 |
| gangrenous mastitis | 5 | 10–1250 |
| healthy cow milk | 10 | <8 µg |

The course of mastitis treatment can be monitored by quantitatively determining the $\alpha_1$-acid glycoprotein values of the milk of cows undergoing treatment for mastitis by the foregoing method. Because the level of $\alpha_1$-acid glycoprotein in the milk more sensitively reflects both the onset and regression of this disease than the serum proteins IgG and albumin, mastitis treatment can be accurately tracked to insure that appropriate medication can be given when required and discontinued when it is no longer required. The effectiveness of the mastitis medication can be improved by withdrawing the medication when it is no longer required. The administration of unnecessary medication can, therefore, be minimized, which reduces the costs of dairy herd management. Moreover, because antibiotics are usually the medication of choice for mastitis, monitoring the $\alpha_1$-acid glycoprotein values of cow milk during mastitis treatment avoids the overuse of antibiotics. This reduces the unnecessary and wasteful use of antibiotics which has generated antibiotic-resistant bacteria. The cost of developing new antibiotics which are effective against these resistant bacteria can be very costly to society. Additionally, minimizing or avoiding the use of antibiotics in the treatment of mastitis and other diseases allows the herd manager to provide the antibiotic-free milk and other products required by regulatory agencies and demanded by health conscious consumers.

EXAMPLE 3

Immediately after birth, the $\alpha_1$-acid glycoprotein levels in piglets are extremely high and gradually decrease to a level approximately twice as high as the normal value determined as described below within the fourth week. An increase in $\alpha_1$-acid glycoprotein is observed at weaning, usually at about 4 weeks, until a peak is reached, usually at about 5 to 8 weeks, and then a gradual decline in $\alpha_1$-acid glycoprotein is observed. Normal values are not reached until about the fifth month after birth. Piglets in groups in which the $\alpha_1$-acid glycoprotein levels did not decline continuously during this time period eventually showed clinical signs of hernia, as well as pneumonia, meningitis and other infectious diseases. Monitoring the $\alpha_1$-acid glycoprotein levels provides the animal manager with a method of evaluating a pig herd to detect the presence of infections and other acute diseases as well as a method for monitoring treatment effects.

The $\alpha_1$-acid glycoprotein levels in the sera of healthy and diseased pigs was measured and compared as follows:

Using the same procedure as in Paragraph A of Example 1, porcine $\alpha_1$-acid glycoprotein was purified, and a goat was immunized by the same procedure as in Paragraph B of Example 1 to produce an antiserum specific for porcine $\alpha_1$-acid glycoprotein.

By the same procedure as described in Paragraph D of Example 1, a reagent for the quantitative determination of porcine $\alpha_1$-acid glycoprotein was prepared, and the quantity of $\alpha_1$-acid glycoprotein was determined in the serum of healthy Landrace pigs and healthy White York pigs as well as pigs diagnosed with the diseases listed in Table 4. The levels of $\alpha_1$-acid glycoprotein in diseased and healthy pigs and the abnormality ratios for each disease are shown in Table 4.

TABLE 4

| Disease | Number of Cases | $\alpha_1$-acid glycoprotein ($\mu$g/ml) | Abnormality (%) |
|---|---|---|---|
| swine dysentery | 2 | 3260, 4485 | 100 |
| exudative dermatitis | 3 | 1880, 2175, 3600 | 100 |
| miscarrying mother pigs | 3 | 480, 520, 870 | 33 |
| multiple abscess | 4 | 1200, 1260 1580, 1620 | 100 |
| pneumonia | 5 | 680, 1125, 1300, 1425, 1580 | 100 |
| meningitis | 8 | 720, 885, 890, 900, 1080, 1260, 1580, 2050 | 100 |
| colibacillemia | 15 | 285, 295, 300, 885, 905, 1000, 1085, 1090, 1255, 1320, 1320, 1425, 1550, 1915, 2280 | 80 |
| healthy Landrace pigs | 10 | 295, 450, 395, 415, 395, 415, 325, 505, 250, 450 | 0 |
| healthy White York pigs | 10 | 295, 435, 415, 415, 435, 360, 500, 280, 435, 360 | 0 |

The upper normal value was regarded as 500 $\mu$g/ml for serum $\alpha_1$-acid glycoprotein in pigs. $\alpha_1$-acid glycoprotein values above 501 $\mu$g/ml were considered to be abnormal and indicative of the presence of disease or homeostatic imbalance. The normal upper limit was computed by the inventor from this and other studies using the mean plus two standard deviations. For healthy swine ranging in age from 4 months to 5 years of age, the serum $\alpha_1$-acid glycoprotein was determined to be 350±89 $\mu$g/ml (n=142), and for healthy swine between 5 and 10 months of age, the serum $\alpha_1$-acid glycoprotein was determined to be 358±79 $\mu$g/ml. No difference in $\alpha_1$-acid glycoprotein level attributable to sex or breed was observed.

When the upper limit of the normal value for porcine serum $\alpha_1$-acid glycoprotein is set at 500 $\mu$g/ml, which is the maximum value for $\alpha_1$-acid glycoprotein for healthy Landrace and White York pigs, 100% of the pigs with swine dysentery, exudative dermatitis, multiple abscess, pneumonia and meningitis exhibited abnormal serum $\alpha_1$-acid glycoprotein levels, even though the number of cases tested was small. Eighty percent of the pigs diagnosed with colibacillemia showed abnormal serum $\alpha_1$-acid glycoprotein levels.

The determination of elevated serum levels of $\alpha_1$-acid glycoprotein has proven helpful to the early detection of diseases, especially acute inflammatory and infectious diseases, or a disturbance in the homeostatic balance in pigs. After a pig has been identified as unhealthy as a result of a serum $\alpha_1$-acid glycoprotein value found to exceed the upper level of normal, the animal can be subjected to such detailed secondary diagnostic methods as clinical, bacteriological, biological and histopathological examinations and image diagnosis. Pigs diagnosed with diseases can then be separated from the rest of the herd or group, if necessary, and treated as required for the disease or condition determined by the specific diagnosis.

Regular monitoring of the $\alpha_1$-acid glycoprotein levels of representative pigs in a herd can provide the farmer, herd manager or veterinarian with important information regarding the relative health or homeostatic balance of the herd. An elevated $\alpha_1$-acid glycoprotein level may be the first indication that an animal's immune system and health has been compromised even though the animal displays no observable symptoms of disease. Procedures such as vaccinations, the administration of drugs, sterilization, and the like can be delayed until $\alpha_1$-acid glycoprotein levels are within normal limits and the animal is clearly at optimum health and well-being and, thus, more likely to tolerate the medication or treatment. Elevated $\alpha_1$-acid glycoprotein levels in a sufficiently large sample of the herd could also indicate that environmental conditions should be carefully evaluated and changed as required to maintain the herd in good health and homeostatic balance. The health status of the herd can also be assessed by monitoring $\alpha_1$-acid glycoprotein levels. This can be particularly useful when the herd has been known to have been exposed or suspected of exposure to infectious agents.

EXAMPLE 4

By the same procedure described in Example 3, the quantity of $\alpha_1$-acid glycoprotein in the serum of 20 pigs introduced to an existing herd was determined by single radial immunodiffusion. This primary screening identified 4 of these pigs to have abnormally high $\alpha_1$-acid glycoprotein values. Secondary diagnostic examinations of these 4 pigs revealed that they had multiple abscesses, meningitis, pneumonia and an infectious disease. Each individual pig was able to be successfully treated as required for its particular disease condition, and all were restored to health.

Often young pigs or pork pigs introduced into a new herd are already suffering from a disease condition that may not be accompanied by observable symptoms. If this is an infectious disease, there is a risk that the disease will be communicated to the rest of the herd. Determination of the $\alpha_1$-acid glycoprotein levels of animals to be added to an existing herd in accordance with the present invention identifies those pigs with elevated $\alpha_1$-acid glycoprotein levels. Secondary diagnosis to identify the specific disease condition from which the animal may be suffering can then be performed and an appropriate treatment instituted. In the past, such animals could not be easily identified until observable symptoms appeared. By that time, the animal had not only infected other animals in the herd, but treatment was not as effective as it would have been if started earlier.

Pigs and other animals are often transported by various shipping methods from one location to another and may frequently be subjected to other changes in their environment, including intermixing litters and different types of management, such as weaning and vaccination timing, that may disturb their homeostatic balance, comprise their health or even cause death. The earliest indication that the pig's or other animal's health may have been compromised or that the immune system has been stressed may be an increase in the level of $\alpha_1$-acid glycoprotein. Consequently, the relative homeostatic or health status of a herd of pigs or other animals that has experienced a change of any kind, including those discussed above, can be ascertained by measuring $\alpha_1$-acid glycoprotein of a statistically representative sample of the herd and comparing the profile of the herd to be evaluated with the $\alpha_1$-acid glycoprotein profile of a normal herd.

The livestock and animal breeding industry has a particular interest in the capability for effectively assessing the health status of swine. As the market prices for pigs continue to increase, the unexpected and often sudden death of apparently healthy newly purchased pigs added to an existing herd increases costs and decreases profits. The method of the present invention enables a stockbreeder or animal manager to evaluate the condition of a pig at the marketplace by determining whether the $\alpha_1$-acid glycoprotein level is normal. The stockbreeder can avoid buying unhealthy animals or animals whose immune systems have been subjected to some unknown stress. In addition, because changes in environment often adversely affect pigs and other livestock, a stockbreeder can monitor the health status of a pig or other animal that appeared healthy when purchased to insure that the animal is managed in a way that will maintain its health and prevent its sudden death. Further, the unnecessary administration of medications such as antibiotics can also be avoided.

EXAMPLE 5

Serum $\alpha_1$-acid glycoprotein in clinically normal newborn colts is undetectable. By one to two weeks after birth, the $\alpha_1$-acid glycoprotein level is 10 to 20 µg/ml and increases continuously during the next 3 months to about 100 µg/ml. Serum $\alpha_1$-acid glycoprotein in pregnant mares increases throughout pregnancy until just after foaling, when the $\alpha_1$-acid glycoprotein level returns to normal. Serum $\alpha_1$-acid glycoprotein values were determined as follows for normal and unhealthy adult horses.

By the same procedure as in Paragraph A of Example 1, $\alpha_1$-acid glycoprotein obtained from horses was purified and used to immunize rabbits by the same procedure as in Paragraph B of Example 1 to obtain an antiserum specific for equine $\alpha_1$-acid glycoprotein.

By the same procedure as in Paragraph D of Example 1, a reagent for the quantitative determination of equine $\alpha_1$-acid glycoprotein was prepared, and the quantity of $\alpha_1$-acid glycoprotein in the serum of healthy horses and horses diagnosed with several disease conditions was determined. The results are shown in Table 5.

TABLE 5

| Diseases | Number of Cases | $\alpha_1$-acid glycoprotein (µg/ml) | Abnormality (%) |
|---|---|---|---|
| pneumonia | 3 | 225, 370, 425 | 100 |
| cardiopathy | 3 | 120, 260, 390 | 67 |
| trauma | 3 | 125, 335, 425 | 67 |
| healthy horses | 6 | 85, 90, 95, 95, 110, 120 | 0 |

A serum $\alpha_1$-acid glycoprotein value above 131 µg/ml was determined to be abnormal in horses.

EXAMPLE 6

By the same procedure as in Paragraph A of Example 1, $\alpha_1$-acid glycoprotein from domestic fowl was obtained, purified and given to rabbits by the same procedure as in Paragraph B of Example 1 to produce an antiserum specific for fowl $\alpha_1$-acid glycoprotein.

By the same procedure as in Paragraph D of Example 1, a reagent for the quantitative determination of $\alpha_1$-acid glycoprotein of domestic fowl was prepared, and the quantity of $\alpha_1$-acid glycoprotein in the serum of healthy and diseased domestic fowl was measured. The results are shown in Table 6.

TABLE 6

| Diseases | Number of Cases | $\alpha_1$-acid glycoprotein (µg/ml) | Abnormality (%) |
|---|---|---|---|
| infectious bronchus | 3 | 420, 865, 945 | 67 |
| staphylococcemia | 3 | 785, 920, 1570 | 100 |
| Marek's disease | 5 | 1030, 1560, 1600, 780, 955 | 100 |
| healthy domestic fowl | 7 | 225, 300, 365, 380, 445, 460, 345 | 0 |

An $\alpha_1$-acid glycoprotein value above 461 µg/ml was determined in accordance with previously described procedures to be abnormal for domestic fowl serum.

EXAMPLE 7

By the same procedure as in Paragraph A of Example 1, $\alpha_1$-acid glycoprotein from dogs was purified, given to rabbits by the same procedure as in Paragraph B of Example 1, and an antiserum specific for canine $\alpha_1$-acid glycoprotein was obtained.

By the same procedure as in Paragraph D of Example 1, a reagent for the quantitative determination of canine $\alpha_1$-acid glycoprotein was prepared, and the quantity of $\alpha_1$-acid glycoprotein in the serum of healthy and diseased dogs was measured. The results are shown in Table 7.

TABLE 7

| Diseases | Number of Cases | $\alpha_1$-acid glycoprotein (µg/ml) | Abnormality (%) |
|---|---|---|---|
| nephritis | 2 | 420, 890 | 50 |
| infectious hepatitis | 3 | 1020, 1560, 1800 | 100 |
| fracture | 3 | 480, 620, 1260 | 67 |
| pyometra | 4 | 1050, 2450, 2500, 2800 | 100 |
| distemper | 5 | 520, 875, 1020, 1540, 1420 | 100 |
| healthy dogs | 12 | 320, 260, 440, 325, 245, 335, 500, 480, 475, 350, 365, 425 | 0 |

A value of $\alpha_1$-acid glycoprotein above 501 µg/ml determined as described above was judged abnormal for $\alpha_1$-acid glycoprotein in dog serum.

Serum $\alpha_1$-acid glycoprotein levels in mongrel dogs was found to be higher than in beagles raised under confined, controlled conditions. $\alpha_1$-acid glycoprotein levels in puppies were significantly lower than in adults. An increase in canine serum $\alpha_1$-acid glycoprotein levels was observed in the diseases above as well as in fetal death, trauma, peritonitis, pneumonia, malignant sarcoma and after experimental surgery. However, in cases where little inflammation is expected, such as external otitis, parasitosis and neuritis, $\alpha_1$-acid glycoprotein levels remained in the normal range. Monitoring the $\alpha_1$-acid glycoprotein levels in dogs treated for cancer is an efficient way to monitor the effectiveness of the treatment.

EXAMPLE 8

By the same procedure as in Paragraph A of Example 1, $\alpha_1$-acid glycoprotein obtained from the serum of cats was purified, given to rabbits by the same procedure as in Paragraph B of Example 1, and an antiserum specific for feline $\alpha_1$-acid glycoprotein was obtained.

By the same procedure as in Paragraph D of Example 1, a reagent for the quantitative determination of feline $\alpha_1$-acid glycoprotein was prepared, and the quantity of $\alpha_1$-acid glycoprotein in the serum of healthy and diseased cats was measured. The results are shown in Table 8.

TABLE 8

| Diseases | Number of Cases | $\alpha_1$-acid glycoprotein ($\mu$g/ml) | Abnormality (%) |
|---|---|---|---|
| leukemia | 2 | 1880, 2050 | 100 |
| suppurative disease | 3 | 420, 1330, 2260 | 67 |
| trauma | 3 | 382, 430, 1420 | 33 |
| purulent pleuritis | 4 | 1120, 1580, 1800, 1850 | 100 |
| panleukopenia | 4 | 885, 1075, 1200, 1580 | 100 |
| healthy cats | 8 | 285, 335, 400, 420, 480, 485, 520, 580 | 0 |

A value of $\alpha_1$-acid glycoprotein of 581 $\mu$g/ml determined as previously described was judged abnormal for feline $\alpha_1$-acid glycoprotein.

No variation in normal feline serum $\alpha_1$-acid glycoprotein levels was attributable to age, gender or breed. One day after birth the $\alpha_1$-acid glycoprotein in kittens was relatively low (50 $\mu$g/ml), but gradually increased up to 6 months of age. Feline serum $\alpha_1$-acid glycoprotein levels increase 2 days after spaying but return to normal by the seventh day without postoperative complications. Feline serum $\alpha_1$-acid glycoprotein levels remain elevated in the presence of inflammation or infectious disease.

EXAMPLE 9

By the same procedure as in Paragraph A of Example 1, $\alpha_1$-acid glycoprotein obtained from the serum of mice was purified, given to rabbits by the same procedure as in Paragraph B of Example 1, and an antiserum specific for mouse $\alpha_1$-acid glycoprotein was obtained.

By the same procedure as in Paragraph D of Example 1, a reagent for the quantitative determination of mouse $\alpha_1$-acid glycoprotein was prepared.

0.1 ml each of $10^5$ tubercle bacilli (BCG) was given intravenously to 5 mice (BALB/c; 8-weeks old, male), blood was collected at varying times, and $\alpha_1$-acid glycoprotein in the serum of the mice was determined by single radial immunodiffusion using the reagent prepared to quantitatively determine mouse $\alpha_1$-acid glycoprotein.

Figure 3:
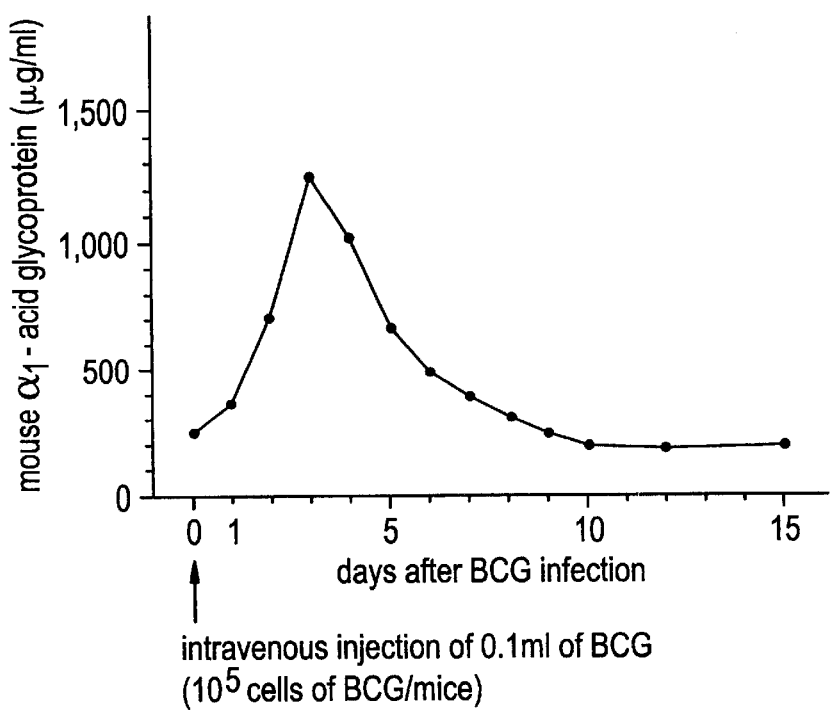
FIG. 3 illustrates fluctuation of $\alpha_1$-acid glycoprotein values in serum of BCG infected mice measured by the diagnostic system of the present invention.

The results are shown in FIG. 3. After the BCG was given, the $\alpha_1$-acid glycoprotein in the blood of the mice increased from the first day, and the maximum value (1300 $\mu$g/ml), was reached on the third day. The $\alpha_1$-acid glycoprotein then decreased and reached a normal value (240±80 $\mu$g/ml) for mouse $\alpha_1$-acid glycoprotein on the ninth day. The $\alpha_1$-acid glycoprotein level of the mice infected with BCG clearly fluctuated during the time the $\alpha_1$-acid glycoprotein levels were monitored. This suggests that the serum $\alpha_1$-acid glycoprotein level is also useful as an indicator to confirm and monitor the biological effects of chemical substances and extracts used for various types of drug efficacy tests.

The method of the present invention has been described as primarily applicable to livestock animals raised for the products which they produce for human consumption and to pets. However, the animal health and well-being assessment method described herein can also be used to determine the $\alpha_1$-acid glycoprotein levels and thus monitor the health and homeostatic balance of any kind of animal or any group of animals. For example, animals such as rats, mice, guinea pigs, monkeys and rabbits which are used as laboratory animals can be monitored according to the present method. This would insure that the test animals are healthy before they are used in a study in which the results could be affected by the health of the animals. In addition, laboratory animal holding and long-term protocols can be assessed. The health status monitoring method of the present invention could also be used by zoo personnel and wildlife park managers to provide objective information on which animal management decisions for the effective management of these types of animal populations can be based. Moreover, the antemortem monitoring of animals intended for slaughter can be performed by the present method to insure that only body parts of healthy animals leave the slaughterhouse. Animal management professionals of all types, from farmers to veterinarians, will find the animal health and homeostatic balance evaluation methods described herein especially useful.

The Examples presented herein demonstrate the usefulness of measuring serum $\alpha_1$-acid glycoprotein levels to determine the health and homeostatic status of various animals and of measuring bovine milk $\alpha_1$-acid glycoprotein levels to identify disease conditions specifically associated with milk production. The $\alpha_1$-acid glycoprotein level can be measured in any type of body fluid, however, including, but not limited to, blood, plasma, serum, urine, milk, cerebrospinal fluid, articular fluid, ascites, thoracic fluid, tears, bile, seminal fluid, mucous and saliva. As a comparison of the $\alpha_1$-acid glycoprotein levels in bovine serum and milk from healthy cattle in Examples 1 and 2 clearly demonstrates, the upper limit of normal will vary, depending on the type of body fluid. Consequently, the normal value for $\alpha_1$-acid glycoprotein in the particular type of body fluid to be evaluated must first be quantitatively determined in animals established to be healthy and a normal upper limit defined as described above. Then the $\alpha_1$-acid glycoprotein value in that particular type of body fluid in each animal to be evaluated can be measured and compared to the normal value.

Animal $\alpha_1$-acid glycoprotein levels increase in response to a variety of stress situations, including trauma and disease. A normal $\alpha_1$-acid glycoprotein level which represents homeostasis and health can be established for adult animals. $\alpha_1$-acid glycoprotein levels differ at birth in different animal species, with some exhibiting high and others low $\alpha_1$-acid glycoprotein values. Animals with high birth levels of $\alpha_1$-acid glycoprotein appear to be more susceptible to opportunistic infections.

Because the amount of circulating $\alpha_1$-acid glycoprotein seems to correlate with the extent of a disease condition or a disturbance in homeostatic balance, the quantitative measurement of animal serum $\alpha_1$-acid glycoprotein values is a useful aid in monitoring the course of the disease or action taken to restore the animal's homeostatic balance.

The monitoring and assessment method of the present invention makes it possible to screen objectively for diseases, especially inflammatory diseases, through the measurement of $\alpha_1$-acid glycoprotein in the body fluids of livestock, pets, animals used for experimental studies and other animals. Because the $\alpha_1$-acid glycoprotein level is usually elevated before observable symptoms appear, the early detection of inflammatory diseases, infectious diseases, malignant tumors and other disease conditions is possible using the method of the present invention. Monitoring $\alpha_1$-acid glycoprotein levels can result in the early detection of an unhealthy condition that may have been missed by a subjective veterinary examination. Although the elevation of $\alpha_1$-acid glycoprotein values above the determined normal value does not specifically identify a particular disease, it is indicative that an animal's immune response is being suppressed as a result of a disease or other stress-producing situation that has disturbed the animal's homeostatic balance.

The animal health monitoring method of the present invention also enables the animal manager to predict the occurrence of disease through regular inspection of $\alpha_1$-acid glycoprotein levels in individual animals or a representative sample of a group. In addition, the animal manager can identify environmental conditions which promote diseases or disturb homeostatic balance, for example confinement at too high a density. The health care of seed or breeding stock can be monitored to insure that these animals remain healthy or can be examined and treated as soon as the $\alpha_1$-acid glycoprotein level is elevated above normal. Moreover, the health status of animals added to an existing group can be evaluated and monitored with the method of the present invention. Vaccinations can be administered when $\alpha_1$-acid glycoprotein levels are normal and the animal's immune system is most capable of optimum response.

The method of the present invention is additionally useful for evaluating the effectiveness of various therapeutic procedures, such as chemotherapy, surgical procedures and the like. In addition, the animal $\alpha_1$-acid glycoprotein monitoring method of the present invention is useful as an indicator for evaluating the prognosis or course of a disease condition or illness in response to drug or other therapy. The administration of unnecessary medications can thus be avoided.

The animal assessment monitoring and method of the present invention is performed most efficiently and effectively with the species-specific diagnostic system prepared as described above and according to the quantitative $\alpha_1$-acid glycoprotein determination method described in Example 1 above. The method of producing the diagnostic system according to the present invention requires a very highly purified animal $\alpha_1$-acid glycoprotein and thus produces a very highly specific anti-animal $\alpha_1$-acid glycoprotein antibody that is highly reliable and can be readily produced in large quantities. Moreover, the cost of producing this very specific antibody is lower than known specific antibody production methods. The diagnostic system produced as described herein can be used to simply and easily determine the $\alpha_1$-acid glycoprotein levels in a large number of specimens. One preferred form the present diagnostic system and $\alpha_1$-acid glycoprotein determination method can take is the specific $\alpha_1$-acid glycoprotein antibody-agar mixture described in the Examples. This mixture is preferably placed in diffusion plates of different sizes that contain different numbers of holes for the specimens to be tested so that the veterinarian or animal manager can select a size suitable for the number of animals to be tested. However, other media that produce results faster may be preferred in some testing applications. Measurement of the $\alpha_1$-acid glycoprotein value in a particular specimen requires only a small quantity of the body fluid to be evaluated, and the quantitative determination of $\alpha_1$-acid glycoprotein values is easily made by comparing the size of the precipitin ring formed to a standard curve. The species-specific $\alpha_1$-acid glycoprotein diagnostic system according to the present invention can be easily packaged in a kit that can be used by animal management personnel in the field to collect and test samples of animal body fluids.

INDUSTRIAL APPLICABILITY

The animal health and homeostatic balance assessment and monitoring method of the present invention will find its primary application in the livestock industry, where it can be used to monitor herd management to achieve greater productivity, to detect early and background disease problems, to monitor the effectiveness of treatment and as a basis for other herd management decisions. Its use as an antemortem screening method will enable animal product inspectors and slaughterhouse managers to insure that only the products of healthy animals enter the market. It will also be a useful health assessment and monitoring method for animal management personnel in any field, from wildlife management to domestic animal veterinary practice.

I claim:

1. A method for controlling the health of a group of animals and maintaining the group of animals in a condition of optimum health to maximize the productivity of the animals in the group, comprising the steps of
    (a) quantitatively determining the normal upper limit for the $\alpha_1$-acid glycoprotein value in a selected body fluid for normal healthy animals of the kind in the group;
    (b) measuring the $\alpha_1$-acid glycoprotein values in said selected body fluid of the animals in the group;
    (c) comparing the measured $\alpha_1$-acid glycoprotein values obtained in step (b) to the normal upper limit determined in step (a);
    (d) identifying the animals in the group with $\alpha_1$-acid glycoprotein values that exceed said normal upper limit;
    (e) using the information obtained in step (d) to assess the relative health of the animals in the group; and
    (f) based upon the assessment of step (e), taking the action required to promote and maintain the optimum health of the animals in the group, thereby maximizing the productivity of the animals in the group.

2. The method described in claim 1, wherein the animals in the group are cattle and the $\alpha_1$-acid glycoprotein values in the serum of the cattle are measured and compared to the normal value for bovine serum $\alpha_1$-acid glycoprotein.

3. The method described in claim 1, wherein the animals in the group are dairy cattle and the $\alpha_1$-acid glycoprotein values in the milk of the cows are measured and compared to the normal value for cow milk $\alpha_1$-acid glycoprotein.

4. The method described in claim 1, wherein the animals in the group are pigs and the $\alpha_1$-acid glycoprotein values in the serum of the pigs are measured and compared to the normal value for porcine serum $\alpha_1$-acid glycoprotein.

5. The method described in claim 1, wherein the animals in the group are horses and the $\alpha_1$-acid glycoprotein value in the serum of the horses are measured and compared to the normal value for equine serum $\alpha_1$-acid glycoprotein.

6. The method described in claim 1, wherein the animals in the group are domestic fowl, and the $\alpha_1$-acid glycoprotein values in the serum of the fowl are measured and compared to the normal value for fowl serum $\alpha_1$-acid glycoprotein.

7. The method described in claim 1, wherein the normal upper limit for the $\alpha_1$-acid glycoprotein value for said healthy animals is determined by measuring the $\alpha_1$-acid glycoprotein values in a selected body fluid in a number of said healthy and homeostatically balanced animals, determining the mean and standard deviation for the measured $\alpha_1$-acid glycoprotein values in said number of animals and designating as the upper limit of normal for $\alpha_1$-acid glycoprotein in the body fluid of said animals the mean value plus two standard deviations.

8. The method described in claim 1, wherein the $\alpha_1$-acid glycoprotein values in said animals are measured by
   (a) obtaining a sample of the selected body fluid from each animal in said representative sample;
   (b) reacting each said sample of body fluid with a diagnostic system specific for the detection of $\alpha_1$-acid glycoprotein in the specific type of body fluid of the specific kind of animal tested to produce a measurable amount of a reaction product that correlates to the amount of $\alpha_1$-acid glycoprotein in said sample; and
   (c) measuring the amount of said reaction product for each sample and comparing said measured amount to a standard curve to obtain a value for the $\alpha_1$-acid glycoprotein in each said sample.

9. The method described in claim 8, wherein said diagnostic system specific for the detection of $\alpha_1$-acid glycoprotein in the specific type of body fluid of the specific kind of animal tested is produced by
   (a) obtaining serum containing $\alpha_1$-acid glycoprotein from an animal of the kind to be tested;
   (b) subjecting said serum to a quaternary purification process including the steps of:
      (i) fractionating said serum with ammonium sulfate to produce an $\alpha_1$-acid glycoprotein precipitate;
      (ii) chromatographically eluting said $\alpha_1$-acid glycoprotein precipitate in a DEAE-cellulose column to produce a first $\alpha_1$-acid glycoprotein fraction;
      (iii) dialyzing said first $\alpha_1$-acid glycoprotein fraction, passing said first fraction through a CM-cellulose column, to obtain a second $\alpha_1$-acid glycoprotein fraction, and dialyzing and freeze-drying said second fraction;
      (iv) eluting said second fraction in a Sephacryl Gel column, collecting a third $\alpha_1$-acid glycoprotein fraction, dialyzing said third fraction with purified water and freeze-drying said dialyzed third fraction to produce a highly purified $\alpha_1$-acid glycoprotein powder;
   (c) injecting said highly purified $\alpha_1$-acid glycoprotein into an animal of a kind different from the kind of animal to be tested to immunize said injected animal and produce antibodies specific for said highly purified $\alpha_1$-acid glycoprotein;
   (d) obtaining serum containing the anti-$\alpha_1$-acid glycoprotein from said immunized animal; and
   (e) combining the antiserum obtained in step (d) with a medium that will allow measurement of the reaction product produced when animal body fluid containing $\alpha_1$-acid glycoprotein is added to the specific antiserum obtained in step (d).

10. The method described in claim 9, wherein in step (e) said specific antiserum is combined with agar, the antiserum-agar mixture is placed in a horizontal diffusion plate, a plurality of holes is formed in said antiserum-agar mixture, said animal body fluid is placed in each of said holes, said reaction product forms a ring around each said hole, and the amount of said reaction product is measured by measuring the diameter of said ring and comparing said diameter to a calibration curve to determine the amount of $\alpha_1$-acid glycoprotein in said sample.

11. The method for controlling and maintaining the health of a group of animals described in claim 1, wherein said $\alpha_1$-acid glycoprotein values are determined by a diagnostic system comprising a reaction medium containing a diagnostic reagent highly specific for $\alpha_1$-acid glycoprotein in said selected body fluid of said animals, body fluid sample receiving means for insuring contact between said body fluid and said diagnostic reagent to allow the $\alpha_1$-acid glycoprotein in the body fluid to react with the diagnostic reagent to produce a visible, measurable reaction product, calibration means for measuring said reaction product to determine the quantity of $\alpha_1$-acid glycoprotein in the sample of body fluid and a normal standard for $\alpha_1$-acid glycoprotein in the body fluid of the kind of animals in the group.

12. The method for controlling and maintaining the health of a group of animals described in claim 11, wherein said reaction medium is agar, said diagnostic reagent is high titer anti-$\alpha_1$-acid glycoprotein highly specific for the kind of animals in the group, said body fluid sample receiving means comprises holes in said reaction medium, said measurable reaction product is a precipitin ring formed in said reaction medium, and said calibration means is a curve correlating the diameter of a precipitin ring with a specific amount of $\alpha_1$-acid glycoprotein.

13. The method for controlling and maintaining the health of a group of animals described in claim 11, wherein said normal standard for $\alpha_1$-acid glycoprotein in a selected body fluid comprises a value obtained by measuring the mean value plus two standard deviations of the $\alpha_1$-acid glycoprotein values in said selected body fluid of a group of animals classified as healthy on the basis of normal clinical and biochemical parameters for said animals.

14. The method for controlling and maintaining the health of a group of animals described in claim 11, wherein said reaction medium, said diagnostic reagent and said body fluid sample receiving means are selected to determine the $\alpha_1$-acid glycoprotein in said body fluid according to an immunological antigen-antibody reaction method selected from the group consisting of single radial immunodiffusion, passive hemagglutination inhibition reaction, enzyme immunoassay and turbidimetric immunoassay.

15. The method for controlling the health of a group of animals described in claim 1, wherein the animals are selected from the group consisting of cattle, pigs, horses, fowl, sheep, goats, dogs, cats, rats, guinea pigs, mice, rabbits and monkeys.

16. A method for evaluating the health status of a group of a selected species of animals whose health status is unknown to determine the health of the group, comprising the steps of
   (a) obtaining the health profile of a reference group of animals of said selected species classified as healthy according to biochemical and clinical parameters by quantitatively determining the $\alpha_1$-acid glycoprotein values in a selected body fluid in a statistically significant representative sample of animals in the reference group;
   (b) measuring the $\alpha_1$-acid glycoprotein values in said selected body fluid in a representative sample of said unknown group of animals to obtain a profile of the health status of said unknown group;
   (c) comparing the unknown group profile obtained in step (b) with the reference group profile obtained in step (a) to assess and determine the health status of said unknown group; and
   (d) using the assessment and determination of health status information of step (c) as a basis for deciding what action is required to insure that the health status of the unknown group is restored to or maintained at an optimum level as indicated by said assessment and taking said required action.

17. A method for managing a group of commercially marketable animals to insure that the animals comprising said group are healthy and remain healthy and commercially marketable, said method including monitoring the $\alpha_1$-acid glycoprotein values in a selected body fluid of said animals, comparing said $\alpha_1$-acid glycoprotein values to a normal $\alpha_1$-acid glycoprotein upper limit determined for the selected body fluid in healthy animals of the same species as said group to identify individual animals with $\alpha_1$-acid glycoprotein values above said normal upper limit, determining the cause of the elevated $\alpha_1$-acid glycoprotein levels, treating said animals as indicated by said cause, monitoring the $\alpha_1$-acid glycoprotein levels of said animals undergoing treatment, and stopping said indicated treatment when the $\alpha_1$-acid glycoprotein levels of said treated animals are demonstrated to be normal.

18. A method for managing a group of commercially marketable animals as described in claim 17, wherein said animals are dairy cattle, said selected body fluid is milk, the cause of the elevated $\alpha_1$-acid glycoprotein levels is bovine mastitis, and said indicated treatment is antibiotic therapy.

19. A method for managing a group of animals as described in claim 17, wherein said animals are pigs, said selected body fluid is serum, the cause of the elevated $\alpha_1$-acid glycoprotein levels is pneumonia, and said indicated treatment is antibiotic therapy.

20. The method of managing a group of commercially marketable animals described in claim 17, wherein said $\alpha_1$-acid glycoprotein levels are monitored with a diagnostic system comprising a reaction medium containing a diagnostic reagent highly specific for $\alpha_1$-acid glycoprotein in said selected body fluid of said animals, body fluid sample receiving means formed in said reaction medium for holding a sample of said selected body fluid in said reaction medium to allow the $\alpha_1$-acid glycoprotein in the body fluid to react with the diagnostic reagent to produce a visible, measurable reaction product, calibration means for measuring said reaction product to determine the quantity of $\alpha_1$-acid glycoprotein in the sample of body fluid and a normal standard for $\alpha_1$-acid glycoprotein in the body fluid of the kind of animals in the group.

21. The method of managing a group of commercially marketable animals described in claim 20, wherein the reaction product is produced by an immunological antigen-antibody reaction selected from the group consisting of single radial immunodiffusion, passive hemagglutination inhibition reaction, enzyme-linked immunoassay and turbidimetric immunoassay.

22. The method described in claim 17, wherein said animals are selected from the group consisting of cattle, pigs, sheep, goats, horses, fowl, dogs, cats, mice, rats, guinea pigs, rabbits and monkeys.

23. A method for maintaining the quality of products obtained from a group of animals at an acceptable level, comprising the steps of (a) obtaining a sample of a selected body fluid from each of the animals in the group;

(b) measuring the $\alpha_1$-acid glycoprotein values in each said sample and comparing the measured $\alpha_1$-acid glycoprotein value with a normal upper limit for $\alpha_1$-acid glycoprotein in said selected body fluid for the kind of animal in the group; and (c) using the products of only those animals in the group whose measured $\alpha_1$-acid glycoprotein values are below said normal upper limit and excluding from use the products of those animals in the group whose measured $\alpha_1$-acid glycoprotein values exceed said normal upper limit.

24. The method for maintaining the quality of products obtained from a group of animals described in claim 23, wherein the animals are selected from the group consisting of cattle, pigs, fowl, sheep and goats.

* * * * *